United States Patent
Hay et al.

(10) Patent No.: US 8,208,699 B2
(45) Date of Patent: Jun. 26, 2012

(54) METHOD AND APPARATUS FOR PREDICTING ENHANCEMENT IN ANGIOGRAPHY

(75) Inventors: Ori Hay, Haifa (IL); Shlomo Gotman, Haifa (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1117 days.

(21) Appl. No.: 12/088,884

(22) PCT Filed: Sep. 14, 2006

(86) PCT No.: PCT/IB2006/053282
§ 371 (c)(1),
(2), (4) Date: Apr. 1, 2008

(87) PCT Pub. No.: WO2007/039838
PCT Pub. Date: Apr. 12, 2007

(65) Prior Publication Data
US 2008/0253634 A1 Oct. 16, 2008

Related U.S. Application Data

(60) Provisional application No. 60/596,590, filed on Oct. 5, 2005.

(51) Int. Cl.
*G06K 9/00* (2006.01)
*A61B 6/00* (2006.01)
(52) U.S. Cl. .............................. 382/128; 382/131; 378/8
(58) Field of Classification Search .................. 382/128, 382/130; 378/4, 8
See application file for complete search history.

(56) References Cited

U.S. PATENT DOCUMENTS

| | | | |
|---|---|---|---|
| 5,459,769 A * | 10/1995 | Brown | 378/4 |
| 5,687,208 A | 11/1997 | Bae et al. | |
| 6,188,744 B1 * | 2/2001 | Shinohara et al. | 378/8 |
| 6,236,706 B1 | 5/2001 | Hsieh | |
| 6,337,992 B1 * | 1/2002 | Gelman | 600/425 |
| 6,470,889 B1 * | 10/2002 | Bae et al. | 604/28 |
| 6,745,066 B1 * | 6/2004 | Lin et al. | 600/425 |
| 2002/0068865 A1 * | 6/2002 | Meaney et al. | 600/415 |
| 2004/0114706 A1 * | 6/2004 | Ikeda et al. | 378/4 |
| 2004/0143185 A1 | 7/2004 | Zatezalo et al. | |
| 2007/0066892 A1 * | 3/2007 | Haras et al. | 600/425 |
| 2007/0255135 A1 * | 11/2007 | Kalafut et al. | 600/431 |

(Continued)

FOREIGN PATENT DOCUMENTS

WO 9712550 A1 4/1997

(Continued)

OTHER PUBLICATIONS

Bae, Peak Contrast Enhancement in CT and MR Angiogrphy: When Does It Occur and Why? Pharmacokinetic Study in a Porcine Model, Radiology, 2003, pp. 809-816.*

(Continued)

*Primary Examiner* — Alexander H Taningco

(57) ABSTRACT

A technique for use in angiography includes obtaining data from a tracking scan following injection of a contrast agent according to a test injection profile. A region of interest (308) is established. The data from the tracking scan, the test injection profile, and the measured enhancement of the region of interest (302) are used to establish a patient function at the region of interest. The patient function and a desired enhancement profile (402) are used to establish a desired clinical injection profile. The desired clinical injection profile is communicated to a contrast injector (36) via an electrical injector interface.

30 Claims, 7 Drawing Sheets

U.S. PATENT DOCUMENTS

2008/0187200 A1* 8/2008 Degani et al. ............. 382/131

FOREIGN PATENT DOCUMENTS

WO      9832376 A1     7/1998
WO      0064353 A2    11/2000

OTHER PUBLICATIONS

Bae, et al., Aortic and hepatic contrast medium enhancement at CT. Part I. Prediction with a computer model, Radiology, 1998, pp. 647-655 vol. 207, Radiological Society of North America.

Hittmair, et al., Contrast optimization in CT angiography, Radiologe, Feb. 1999, pp. 93-99, vol. 39 No. 2, Universitatsklinik fur Radiodiagnostik, Wien.

Fleischmann, et al., Mathematical analysis of arterial enhancement and optimization of bolus geometry for CT angiography using the discrete fourier transform, Journal of Computer Assist Tomography, May-Jun. 1999, pp. 474-484, vol. 23 No. 3, Lippincott, Williams & Wilkins, Inc., Philidelphia.

Fleischmann, et al., Improved Uniformity of Aortic Enhancement with Customized Contrast Medium Injection Protocols and CT Angiography, Radiology, Feb. 2000, pp. 363-371, vol. 214 No. 2, Radiological Society of North America.

Jang, et al., Hepatocellular Carcinoma: Are Combined CT during Arterial Portography and CT Hepatic Arteriography in Addition to Triple-Phase Helical CT All Necessary for Preoperative Evaluation?, Radiology, May 2000, pp. 373-380, vol. 215 No. 2, Radiological Society of North America.

Bae, et al., Multiphasic Injection Method for Uniform Prolonged Vascular Enhancement at CT Angiography: Pharmacokinetic Analysis and Experimental Procine Model, Radiology, Sep. 2000, pp. 872-880, vol. 216 No. 3, Radiological Society of North America.

Foley, et al., Multiphase Hepatic CT with a Multirow Detector CT Scanner, AJR, Sep. 2000, pp. 679-685 vol. 175, American Roentgen Ray Society.

Hittmair, et al., Accuracy of predicting and controlling time-dependent aortic enhancement from a test bolus injection, Journal of Computer Assist Tomography, Mar. 1, 2001, pp. 287-294, vol. 25 No. 2, University of Radiology, university of Vienna, Vienna, Austria.

Zaky, et al., Triphasic Spiral CT in Hepatocellular Carcinoma Timing Optimization doe Increasing Detectability, Journal of the Egyptian Nat. Cancer Inst., Mar. 2001, pp. 49-56, vol. 12 No. 1, The Departments of Radiodiagnosis, NCI, Faculty of Medicine, Cairo and Benha Universities.

Karahan, et al., Characterization of Hepatocellular Carcinomas with Triphazic and Correlation with Histopathologic Findings, ACTA Radiologica, 2003, pp. 566-571, vol. 44, Denmark.

Francis, et al., Multidetector CT of the Liver and Hepatic Neoplasms: Effect of Multiphasic Imaging on Tumor Conspicuity and Vascular Enhancement, AJR, May 2003, pp. 1217-1224, vol. 180 American Roentgen Ray Society.

Brink, Contract optimization and scan timing for single and multidetector-row computed tomography, Journal of Computer Assist Tomography, May-Jun. 2003, pp. S3-8, Suppl 1, Department of Diagnostic Radiology, Yale University School of Medicine, New Haven, CT.

Silverman, MSCT: Implications for Liver Imaging, Nov. 2003, www.imagingeconomics.com/library/200311-14.asp.

Saini, et al., Contrast techniques for hepatic multidetector CT angiography, Supplement to Applied Radiology, Dec. 2003, pp. 29-33.

Itoh, et al., Multiphase Contrast-enhanced CT of the Liver with a Multislice CT scanner: Effects of Iodine Concentration and Delivery Rate, Radiation Medicine, 2005, pp. 61-69, vol. 23, No. 1.

Philips Medical Systems (Cleveland), Inc., Brilliance CT Instructions for Use, 2005, 12 pages, vol. 1, Chapter 10 Bolus Tracking.

Cademartiri, F., et al.; Parameters Affecting Bolus Geometry in CTA: a review; 2002; JCAT; pp. 598-607.

* cited by examiner

METHOD AND APPARATUS FOR PREDICTING ENHANCEMENT IN ANGIOGRAPHY

CROSS REFERENCE TO RELATED APPLICATIONS

This application claims the benefit of U.S. provisional application Ser. No. 60/596,590 filed Oct. 5, 2005, which is incorporated herein by reference.

The present invention relates to the contrast enhanced angiography, and to the predication of contrast enhancement rate in angiographic images. It finds particular application to computed tomography (CT) angiography, and also has application to angiography in magnetic resonance imaging and other modalities.

Contrast agent injection timing remains a challenging facet of CT Angiography (CTA). Unlike conventional angiography where the arterial enhancement is characterized by a narrow and tall contrast enhancement curve, it is difficult to achieve a uniform enhancement profile in CTA.

In general, the arterial enhancement in CTA exams can be modulated by adjusting the total amount of iodinated contrast material, the intravenous injection rate (volume of contrast agent/unit of time), and the scan delay. However, the vascular time-attenuation response to an intravenous contrast agent injection is influenced by patient-specific physiologic characteristics. Even for a particular patient, these characteristics can change with time. As a result, there is uncertainty in the expected arterial enhancement in terms of magnitude, uniformity of enhancement over time, and time interval between the beginning of a contrast agent injection and the appearance of contrast agent in the vascular region of interest.

Insufficient arterial enhancement may result in less than optimal or even non-diagnostic image quality. Excessive enhancement, on the other hand, is diagnostically unnecessary, wastes contrast material, may have deleterious effects on the patient, and may cause artifacts.

The ability to predict and to control arterial enhancement in CTA has been the focus of recent research on the underlying physiologic and pharmacokinetic principles. Bae et al. and Fleischmann et al. have successfully predicted arterial enhancement in a patient by using a test bolus injection and mathematical models.

Fleischmann regards the patient as a whole as a complex system. The system is described mathematically by its effect (the "patient function") on the input function (the contrast agent injection) to become the output function (the time-enhancement response). Bae regards the patient as set of compartments, each with different parameters regarding its input and capacity. Both techniques assume a linear and time-invariant model, and use mathematical deconvolution methods such as the Fourier transform or the Z transform to analyze and describe such a complex system as a black box. See Fleischmann et al., *Mathematical Analysis of Arterial Enhancement and Optimization of Bolus Geometry for CT Angiography Using the Discrete Fourier Transform*, Journal of Computer Assisted Tomography, 23(3):474-484 (1999); Bae et al., *Multiphasic Injection Method for Uniform Prolonged Contrast Enhancement at CT Angiography: Pharmacokinetic Analysis and Experimental Porcine Model*, Radiology 2000; 216:872-880.

In addition, various techniques for conducting CTA studies have been implemented. These techniques typically include an optional surview scan which is used to determine the axial location of the region of interest (ROI). In a fixed delay method, contrast is injected into the patient and the scan is initiated after a predefined delay. In a bolus tracking method, the desired axial location is scanned and the ROI is marked. Contrast is then injected, and a series of low dose scans is obtained at the axial location. When the contrast agent is detected at the ROI at a desired enhancement level, a diagnostic scan is triggered. In a test injection method, the desired axial location is scanned and the ROI is marked. A relatively small amount of contrast is injected, and a series of low dose axial scans are obtained. Information from the test scan is used to calculate a scan delay. Contrast is injected using a predefined injection protocol, and the scan is initiated after the calculated delay.

While these techniques have proven useful, there remains room for improvement. For example, the fixed delay method has limited ability to account for physiological variations. These techniques have also required a manual or offline determination of injection protocols, as well their manual entry into the injector. The test injection has also required the use of an offline application to evaluate the information from the test scans.

Moreover, these techniques have provided limited ability to obtain multiphasic scans of the anatomy. It has been necessary to administer a contrast agent injection followed by a scan of the relevant region of the patient's anatomy to obtain scan data for each phase of contrast enhancement. This process has been repeated for the desired phases. In addition to requiring multiple scans of the patient, it has been necessary to register the various scans and account for gross patient motion and periodic motion due to respiration and other factors. These steps add complexity to the workflow and are a source of errors and inaccuracies.

Accordingly, it is desirable to provide an improved method for predicting contrast agent enhancement and determining desired injection protocols. It would also be desirable to reduce the complexities resulting from multiple scanning operations.

Aspects of the present invention address these matters and others.

According to a first aspect of the present invention, a method includes defining first and second regions of interest of the anatomy of a patient; establishing a first desired time enhancement profile at the first region of interest and a second desired time enhancement profile at the second region of interest; and establishing a desired injection profile for administering contrast agent to the patient. The desired injection profile is established based on the first and second desired time enhancement profiles, a first injection profile used to administer contrast agent to the patient, and measured time enhancement profiles at the first and second regions of interest resulting from the administration of the contrast agent to the patient according to the first injection profile.

According to a more limited aspect, the invention includes defining a third region of interest of the anatomy of the patient, establishing a third desired time enhancement profile at the third region of interest, and establishing the desired injection profile based on the third desired time enhancement profile and a measured time enhancement profile at the third region of interest resulting from the administration of the contrast agent to the patient.

According to another more limited aspect of the invention, the method includes using electrical signals to communicate the desired injection profile to a power contrast injector.

According to still another limited aspect, establishing a desired injection profile for administering contrast agent to the patient includes establishing a desired injection profile for enhancing the first region of interest, and establishing a desired injection profile for enhancing the second region of interest.

According to a yet more limited aspect, the desired injection profile for administering contrast agent to the patient is a multiphasic injection profile which includes the desired injection profile for enhancing the first region of interest and the desired injection profile for enhancing the second region of interest.

The phases of the multiphasic injection profile may be coordinated so that the desired enhancements of the first and second regions of interest are predicted to occur at approximately the same time.

According to another more limited aspect, the method includes administering contrast agent to the patient according to the first injection profile, and obtaining a plurality of images of the first and second regions of interest including an enhancement resulting from the administration of the contrast agent according to the first injection profile. The first and second regions of interest may be segmented based on the enhancement resulting from the contrast agent. Moreover, the desired enhancement profiles may be established so that the first and second regions are enhanced, but to a different degree.

According to another aspect of the present invention, a method includes administering contrast agent to a patient according to a test injection profile, obtaining a tracking scan of the patient's anatomy, defining a first region of interest of the patient's anatomy, using the plurality of temporally spaced images to generate a first enhancement profile at the first region of interest, establishing a first desired injection profile for administering contrast agent to the patient, predicting an enhancement of the first region of interest resulting from the first desired injection profile, communicating the first desired injection profile to an injector via electrical signals, administering contrast agent to the patient according to the first desired injection profile, and obtaining a scan of the patient's anatomy.

According to another aspect of the present invention, a computer readable storage medium contains instructions which, when executed by a computer, cause the computer to carry out a method which includes defining a first region of interest of a patient's anatomy, generating a first measured time enhancement profile at the first region of interest based on a plurality of temporally spaced images of the patient's anatomy obtained following an injection of contrast agent according to a test injection profile, establishing a first desired time enhancement profile at the first region of interest, establishing a desired injection profile for administering contrast agent to the patient, and communicating the desired injection profile to an injector via an electrical signal. The desired injection profile is established based on the first desired time enhancement profile, the test injection profile, and the first measured time enhancement profile.

Those skilled in the art will appreciate still other aspects of the present invention upon reading and understanding the attached description.

Figure 1:
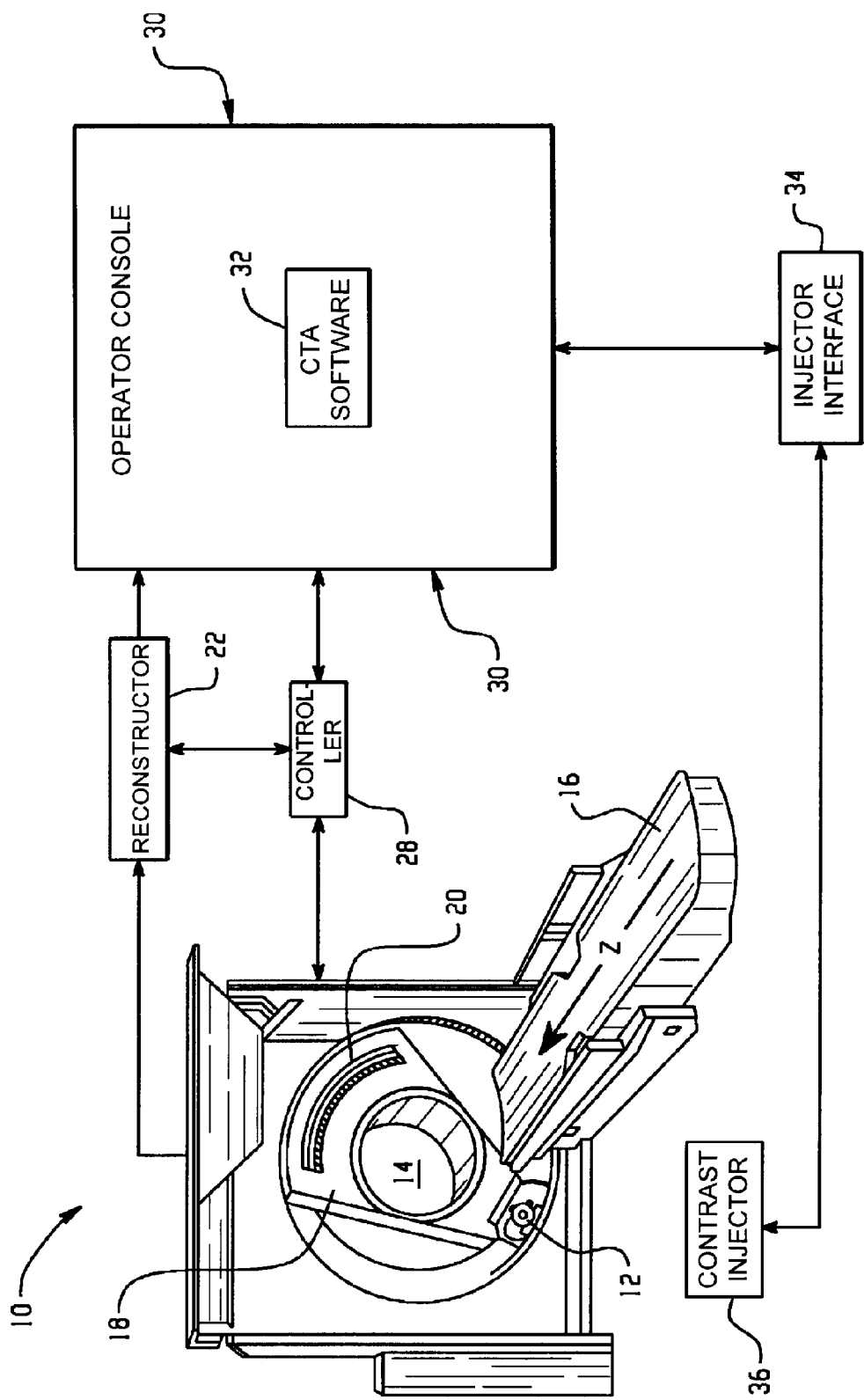
FIG. 1 depicts a CT imaging system and contrast injector.

With reference to FIG. 1, a CT scanner 10 includes a rotating gantry 18 which rotates about the z-axis. The gantry 18 supports an x-ray source 12 such as an x-ray tube. The gantry 18 also supports an x-ray sensitive detector 20 which subtends an angular arc on the opposite side of an examination region 14. X-rays produced by the x-ray source 12 traverse the examination region 14 and are detected by the detector 20.

In one embodiment, the detector 20 is a multi-slice detector which includes more than one row of detectors extending in the z-direction. Flat panel or other detector 20 configurations may also be implemented. Depending on the configuration of the detector 20, the x-ray source 12 generates a generally fan, wedge, or cone shaped radiation beam. Moreover, a so-called fourth generation scanner configuration, in which the detector 20 spans an arc of 360 degrees and remains stationary while the x-ray source 12 rotates, may also be implemented.

A patient support 16 such as a couch supports the patient in the examination region 14. The patient support 16 is preferably movable in the z-direction. A controller 28 coordinates the various scan parameters as necessary to carry out a desired scan protocol. In a helical scan, movement of the support 16 and the gantry 18 are coordinated along with such that the x-ray source 12 and the detectors 20 traverse a generally helical path with respect to the patient. In an axial scan, the position of the support 16 remains constant while the source and detector rotate about the patient. The x-ray source parameters such as x-ray tube voltage and current are likewise maintained at values appropriate for a desired protocol.

Data collected by the detector 20 is processed by a reconstructor 22 to generate volumetric data indicative of the interior anatomy of the patient.

A general purpose computer serves an operator console 30. The console 30 includes a human readable output device such as a monitor or display and an input device such as a keyboard and mouse. Software resident on the console allows the operator to control the operation of the scanner 10 by establishing desired scan protocols, initiate and terminate scans, view and otherwise manipulate images and other data from the scans, and otherwise interact with the scanner 10. The software, which is implemented by way of computer readable instructions stored on a computer readable medium accessible to the console 30, includes CTA software 32 which is executed by one or more computer processors associated with the console 30.

An injector interface 34 provides an interface between the scanner 10 and a contrast injector 36. The interface 34 preferably operates via the known controller area network open (CANopen) interface standard, and more particularly CiA 425, the CANopen application profile for medical diagnostic add-on modules, to provide bidirectional electrical communications between the injector 36 and the scanner 10, although other suitable standard or proprietary interfaces may be used.

The injector 36 is a power contrast injector which preferably includes multiphasic injection and saline flush capabilities. In addition, the injector 36 preferably includes a class 4 interface, which allows the injector 36 to be operated by the scanner 10 so that injection parameters may be communicated to the injector 36 and injections started and stopped via the interface 34. Likewise, real time and final injection parameters (e.g., flow rate, volume, and pressure) may be communicated from the injector 36 to the scanner 10 via the interface.

Figure 2:
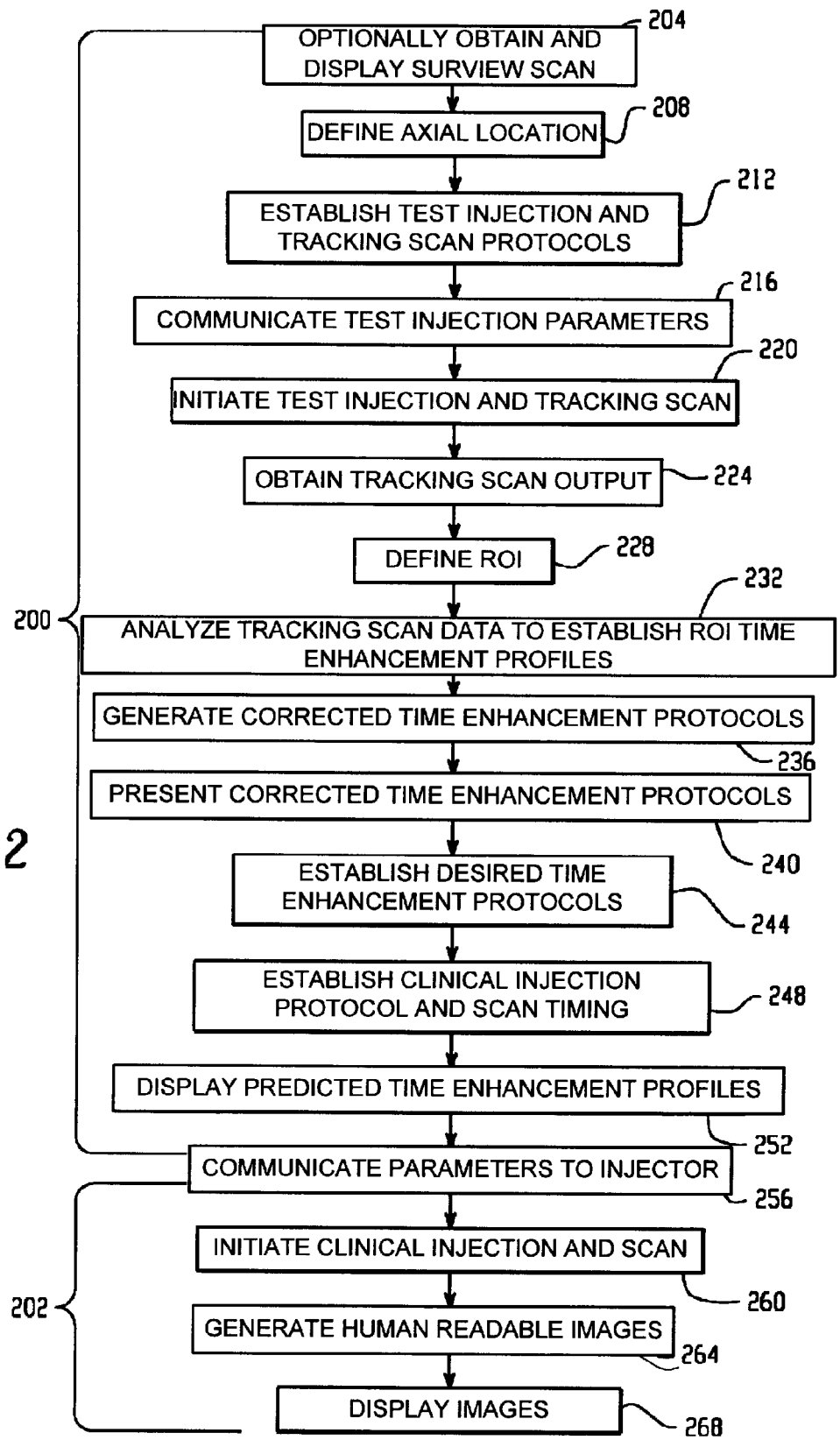
FIG. 2 depicts a technique for predicting enhancement.

Turning now to FIG. 2, operation of the CTA software 32 can be generally characterized as having a pre-scan phase 200 and a clinical scan phase 202.

In the pre-scan phase 200, an optional surview scan is obtained at 204 and displayed on the console 30. At 208, the operator uses the surview scan to define an axial location to be tracked following a test injection.

At 212, the test injection and tracking scan protocols are established. The operator is prompted to specify information relating to the desired test injection, including the volume of the agent to be administered, its concentration, and the injection rate. In one embodiment the injection rate is substantially constant over the injection period. Where the injector has the capability to provide a saline chaser, the operator is prompted to enter the saline volume and flow rate.

The operator is also prompted to specify the tube voltage and current, the cycle time for the tracking scan, the delay from the beginning of the test injection to the start of the tracking scan, and the tracking scan duration. The tracking scan includes a time series of axial scans at the axial location. The cycle time (sampling rate) specifies the time period between the start of each scan in the series.

As particular users tend to have preferred injection and scan protocols, it is generally advantageous to store one or more of the parameters as default values rather than to require the operator to re-enter the values for each scan. The operator is then asked to confirm the default values or otherwise to change as required for a particular situation.

The accuracy of the enhancement prediction is improved by obtaining a more accurate measurement of the enhancement resulting from the test injection. The scan delay and scan length should be selected to capture the entire test injection enhancement profile—i.e. capturing the upslope and the entire test injection enhancement tail. The tail, which plays a significant role in the prediction, may continue for some time after the peak enhancement is reached. Using a saline flush shortens the enhancement tail, and thus reduces the required scan length.

Prediction accuracy is also enhanced by selecting a suitable cycle time. The cycle time should be adapted to the test injection profile, vessel being scanned and the clinical scan type. For example, the cycle time can be relatively longer for larger volumes and a slower flow rate. Similarly, the cycle time can be relatively longer where the vessel scanned is relatively far from the injection location (e.g., the abdominal aorta and iliacs), and relatively shorter where the vessel scanned is near the injection location (e.g., for pulmonary embolisms). Where the clinical scan is relatively shorter and more accurate, the cycle time should likewise be shorter.

The test injection volume should be large enough so that the contrast material does not become diluted in the blood, which can result in a relatively poor enhancement profile.

In one example, a suitable tracking scan is a relatively low dose (20-30 mA, 120 kVp) axial scan with a cycle time of 0.7-2.5 seconds and a duration of 20-60 seconds, depending on the vessel, injection and scan type as describe above. A suitable test injection includes about 10-15 cc of iodinated contrast material at a rate of 4-6 cc/sec using a dual head injector with saline chaser. In the case of a single head injector, 10-20 cc of contrast at a rate of 3-6 cc/sec may be used. When a test injection with smaller flow rates (2-3.5 cc/sec) is used, the contrast agent tends to dilute more in the blood thus a larger total amount of contrast is required.

At 216, the test injection parameters are communicated to the injector 36 via the injector interface 34. Alternately, the operator may manually enter the relevant parameters into the injector 36 using the injector's operator interface.

The test injection and tracking scan are initiated at 220. The operator enters a tracking scan start command via the console 30, and a corresponding injector start command is communicated to the injector 36 via the injector interface 34. After the scan delay, the tracking scan is initiated and obtained using the tracking scan protocol at 224. The output of the tracking scan is a time series of axial images at the desired axial location which show the enhancement resulting from the contrast agent injection as a function of time.

At 228, one or more ROIs are defined. More particularly, an axial image from the tracking scan is displayed, and the operator is asked to click on the desired region or regions of interest. Depending on the clinical application, the ROIs are typically a point or region in the lumen of blood vessels of interest. The operator is also prompted to designate each ROI as an enhanced ROI in which contrast enhancement is desired in the clinical scan data or as a non-enhanced ROI in which contrast enhancement is not desired. Rather than requiring an explicit selection by the operator, one or more of the ROIs may also be identified and/or designated automatically using appropriate image analysis techniques.

At 232, the data from the tracking scan is analyzed to establish a time enhancement profile for each ROI. More particularly, the CTA software 32 samples the tracking scan data at the coordinates of each ROI to determine the enhancement as a function of time for each.

The 236, corrected time enhancement profiles are generated for each ROI. The time enhancement profile for each ROI generated at step 232 is fitted to an ideal time enhancement curve to correct for noise and recirculation in the tracking scan data. For iodine contrast media, the time enhancement curve for large vessels can be modeled by a gamma variant fit of the form $$C_a(t) = k(t)^a e^{t/b} \qquad \text{Equation [1]}$$

where C is the attenuation above the vessel baseline, t is time, and k, a and b are parameters of the fit. It is also necessary to shift the time to the arrival time and multiply by a constant since this curve has integral of one, thus its peak is less than one and it is desirable to have larger peak values.

Figure 3:
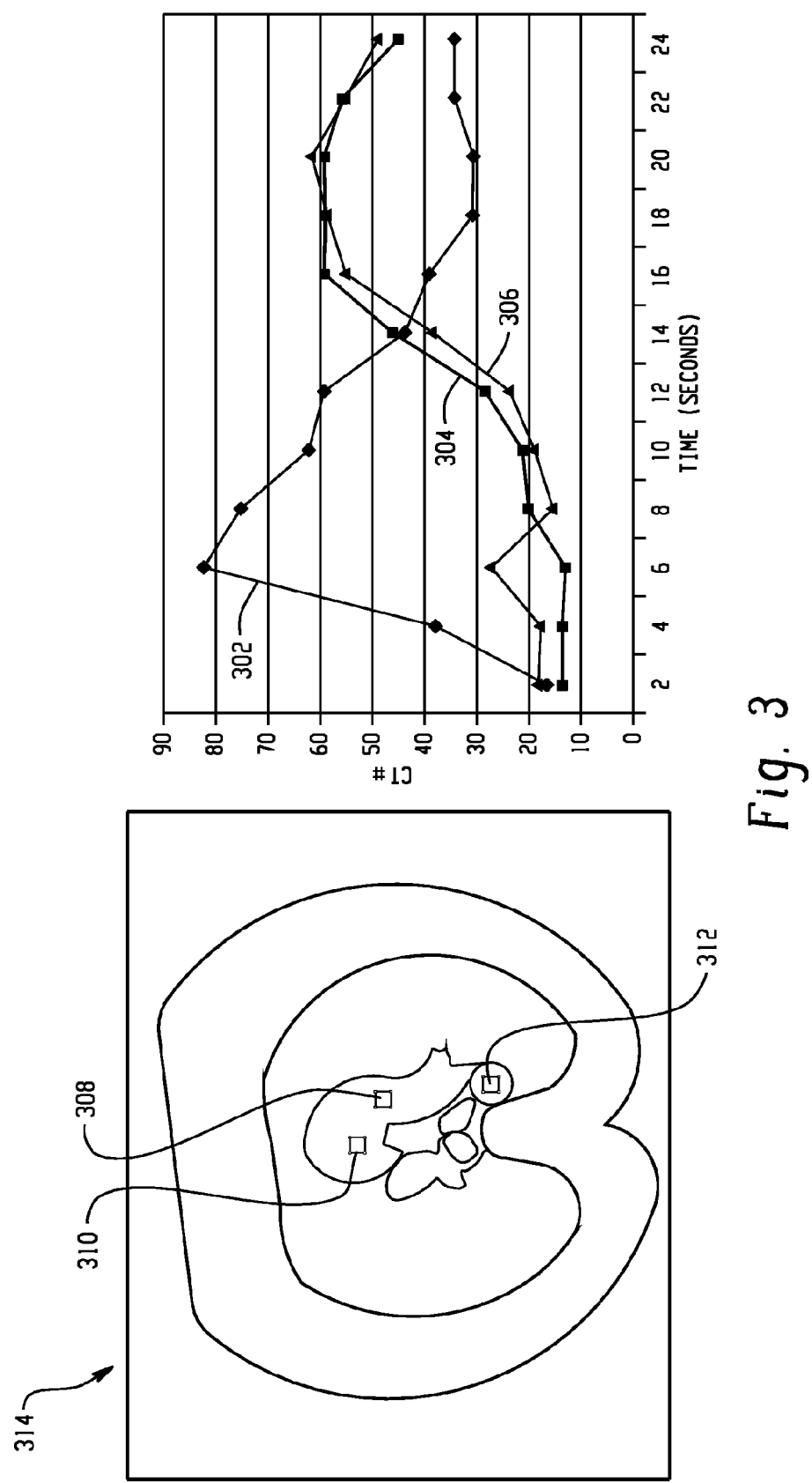
FIG. 3 depicts information presented to an operator in connection with a tracking scan.

At 240, and with reference to FIG. 3, which shows an exemplary tracking scan with three (3) ROIs, the corrected time enhancement profile 302, 304, 306 for each ROI is presented to the operator in graphical form via the console 30. The locations of the corresponding ROIs 308, 310, 312 are likewise depicted on an axial image 314 from the tracking scan. If the ROIs 308, 310, 312 and corresponding time enhancement profiles 302, 304, 306 are acceptable to the operator, the process proceeds to the next step. If not, the operator may return to step 228 to alter one or more of the ROIs.

Figure 4:
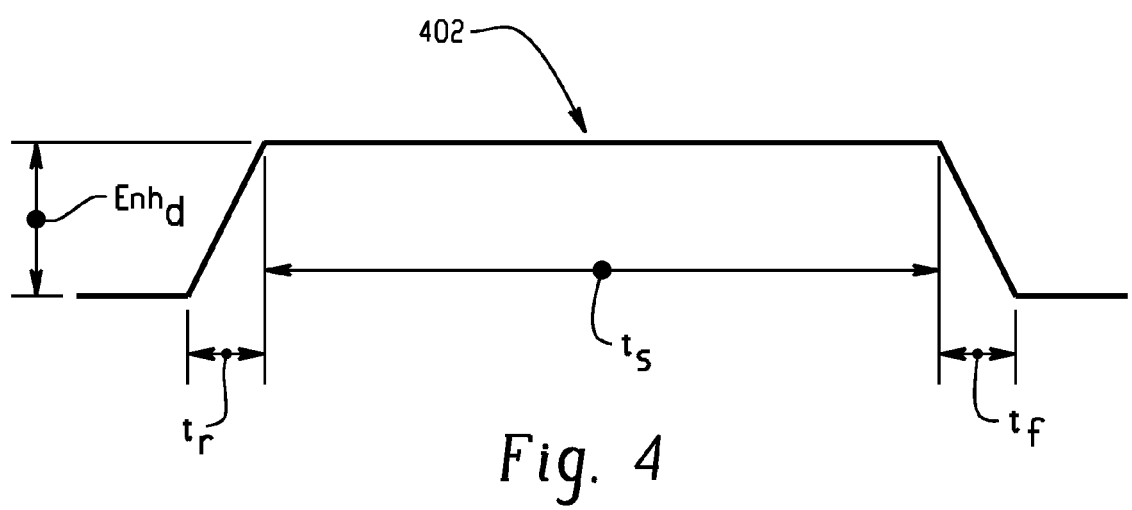
FIG. 4 depicts a desired enhancement curve.

At 244, and with reference to FIG. 4, the desired time enhancement profile(s) 402 for the clinical scan are established. In one embodiment, the operator is presented with a default value for the desired enhancement $Enh_d$ for the enhanced ROI(s), which is presumed to be constant during the scan. If necessary, the operator is given the opportunity to change the value. Alternately, time varying enhancements may also be implemented. It may also be desirable to establish a different desired enhancement for each ROI. If the ROI is a non-enhanced ROI, the time enhancement profile 402 is established at or near the baseline (non-enhanced) value.

The time required to perform the clinical scan $t_s$ is automatically determined based on the desired scan protocol for the clinical scan. To avoid discontinuities in the injection calculation caused by abrupt changes in the desired time enhancement profile 402, a rise time $t_r$ and fall time $t_f$ are provided at the beginning and end of the profile 402.

The clinical injection profile and scan timing are established at 248. In the following discussion, which generally follows the model discussed by Fleischmann et al., enhancement is denoted as Enh, the contrast agent injection flow rate is denoted as Inj, and the patient function is depicted as Pat. Physically, Pat represents the reaction of the patient system to a Dirac impulse at the input.

The enhancement (Enh) is the convolution of the contrast agent injection rate (Inj) and the individual patient (Pat) function. Writing this using a Discrete Fourier transform, we end up with a linear relationship in Fourier space (FS):

$$Enh(\tau) = Pat(\tau) \cdot Inj(\tau) \qquad \text{Equation [2]}$$

Applying the values from the test injection and tracking scan 220 for a particular ROI yields the subject's patient function at that ROI:

$$Pat = \frac{Enh_{test}}{Inj_{test}} \qquad \text{Equation [3]}$$

where $Enh_{test}$ is the Fourier transformed enhancement from the tracking scan at the particular ROI, and $Inj_{test}$ is the Fourier transformed test injection profile.

Once the patient function is known, the enhancement resulting from an arbitrary contrast agent injection can be determined:

$$Enh_{ideal} = Pat \cdot Inj_{ideal} \qquad \text{Equation [4]}$$

where $Enh_{ideal}$ is the Fourier transformed predicted enhancement profile at the particular ROI. An inverse DFT is applied to the result of equation [4] to obtain the predicted ideal enhancement profile following the specified injection in the time domain. Equation [4] can also be used to obtain the injection required to reach the desired time enhancement curve 402 at the ROI. The Fourier spectrum of the flow rate for an ideal injection is expressed as:

$$Inj_{ideal} = \frac{Enh_d}{Pat} \qquad \text{Equation [5]}$$

The ideal injection protocol (i.e. the injection flow profile as a function of time) that produces the desired enhancement at the ROI is calculated again by back-transforming the result of equation [5] into the time domain. A fitting algorithm is then used to generate a multiphasic clinical injection profile which is consistent with the capabilities of the injector 36.

The predicted clinical enhancement profile is obtained by applying the calculated clinical injection protocol to equation [5] and back transforming into the time domain.

While the above discussion has focused on a model similar to that disclosed in Fleischmann, other suitable models, such as the model disclosed in Bae, may also be implemented.

The scan delay is determined by locating an enhancement peak which has the desired enhancement for the scan duration, and establish the desired scan duration around the peak. The scan delay is the time period between the injection and the beginning of the scan.

Where multiple ROIs are selected, each ROI is designated as either to be enhanced or non-enhanced in the clinical scan. A desired injection profile and scan delay are established as described above for each ROI. A multiphasic injection is planned, with the sequence of the injections staggered so that the injection with the longest scan delay is performed first, the injection with the next shorter scan delay is performed next, and so on. The delay between the respective injections of the multiphasic injection are selected so that the respective ROIs are predicted to be enhanced at approximately the same time. Consequently, the desired enhancement at each ROI can be obtained in a single scan.

Figure 7A:
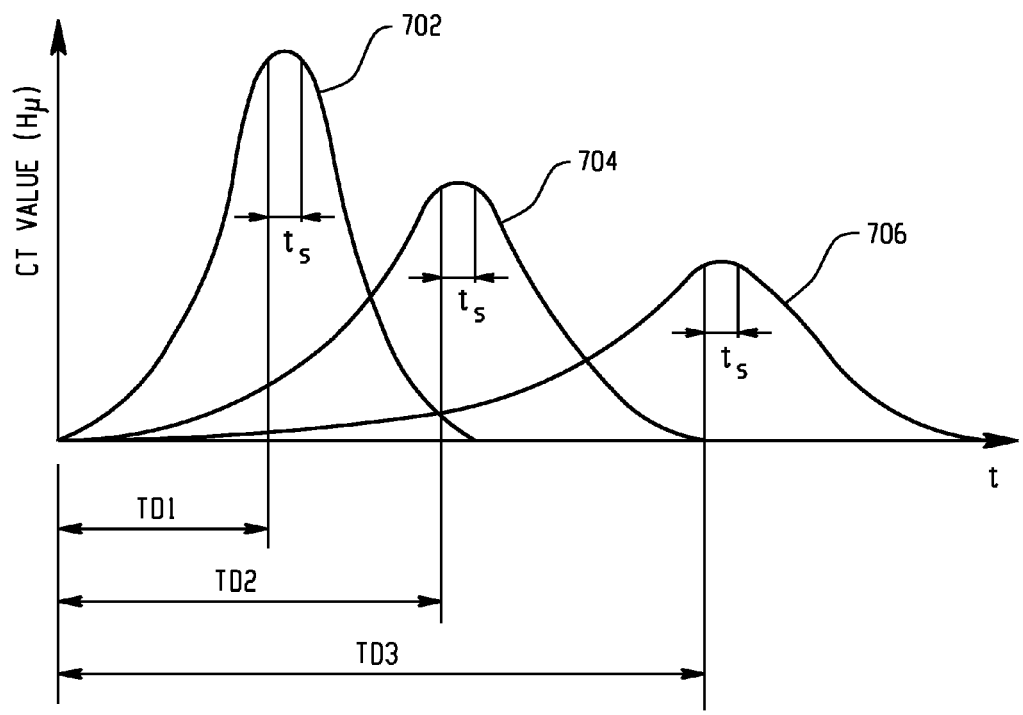
FIG. 7a depicts exemplary predicted time enhancement profiles for three regions of interest.
Figure 7B:
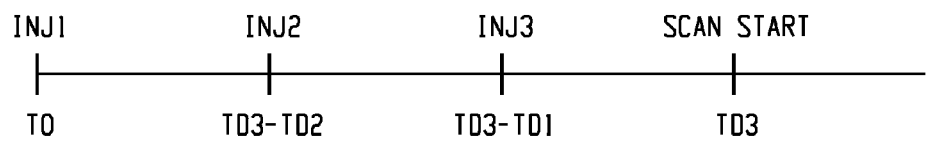
FIG. 7b depicts a timeline for a triphasic injection followed by a single scan.

This process is illustrated at FIGS. 7a and 7b. FIG. 7a depicts exemplary predicted time enhancement profiles for three ROIs 702, 704, 706. The proposed scan time $t_s$ s indicated with respect to each ROI. The calculated scan delay for the first ROI 702 is depicted as TD1, the calculated scan delay for the second ROI 704 is depicted as TD2, and the calculated scan delay for the third ROI 706 is depicted as TD3. With reference to FIG. 7b, the injection corresponding to the third ROI 706 is initiated at time T0, the injection corresponding to the second ROI 704 is initiated at time TD3-TD2, and the injection corresponding to the first ROI is performed at time TD3-TD1. The scan is initiated at time TD3.

In the case of a non-enhanced ROI the respective scan delays are shortened to minimize the amount of contrast which reaches the non-enhanced ROI. If the desired enhancement cannot be achieved by lengthening or shortening the scan delay, the operator is so advised and provided the opportunity to enter revised input parameters.

Figure 5:
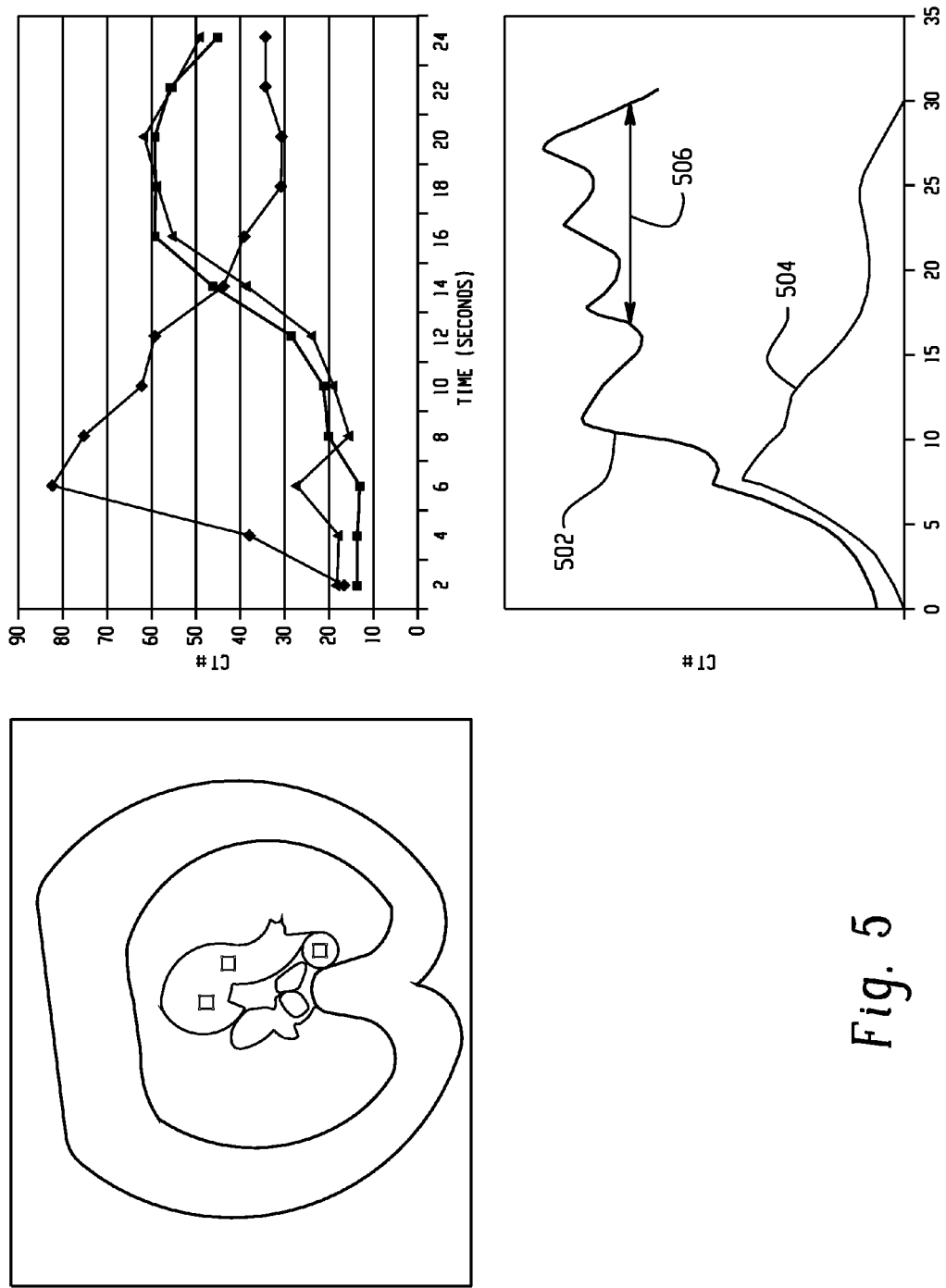
FIG. 5 depicts information presented to an operator for planning a clinical scan.
Figure 6:
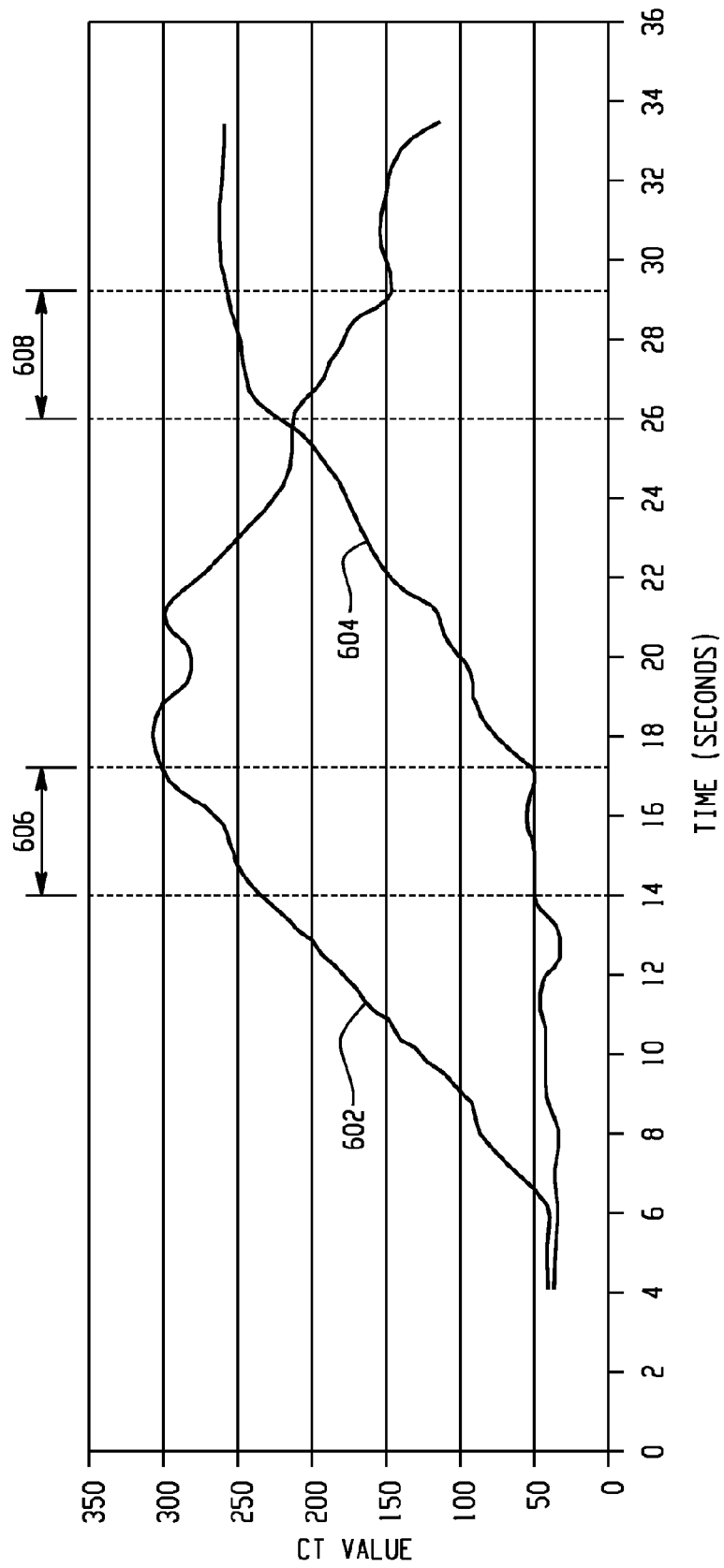
FIG. 6 depicts exemplary predicted time enhancement profiles for two regions of interest.

At 252, the predicted time enhancement profile(s) are displayed on the console. With reference to FIG. 5 in the case of a single selected ROI, the predicted time enhancement profile 502 and the corrected time enhancement profile from the test injection 504 for the selected ROI is displayed on the console 30. The proposed clinical scan timing 506 is also displayed in graphical form in relation to the predicted enhancement profile 502. The calculated clinical injection parameters, the calculated delay to the start of the clinical scan, the predicted minimum enhancement during the scan, together with the information depicted in connection with FIG. 3 are presented to the operator via the console 30. If desired, the operator is also given the opportunity to manually adjust the scan delay, with the adjusted scan timing preferably displayed graphically in relation to the predicted time enhancement profile 502. If the parameters are suitable, the operator may accept them. If not, the operator is given the opportunity to alter the desired clinical enhancement or select a different scan protocol, in which case step 248 is repeated with the new values.

Where multiple ROIs are selected, it is advantageous to display the predicted time enhancement profile for each ROI. FIG. 6 depicts exemplary predicted time enhancement profiles 602, 604 for the pulmonary artery and the aorta, respectively. Again, it is desirable to present the calculated scan timing graphically in relation to the predicted time enhancement profiles. Where the operator has designated the pulmonary artery as an enhanced ROI and the aorta as a non-enhanced ROI, a scan conducted at 606 would be expected to provide preferential enhancement of the pulmonary artery. Where the operator has designated both the pulmonary artery and the aorta as an enhanced ROIs, a scan conducted at 608 would provide enhancement of both. Again, the operator is preferably provided the opportunity to adjust the scan delay.

At 256, the clinical injection parameters are communicated to the injector 36 via the injector interface 34. Alternately, the operator may manually enter the relevant parameters into the injector 36 using the injector's operator interface.

The clinical injection and scan are initiated at 260. Upon receiving a clinical procedure start command from the operator, an injector start command is communicated to the injector 36 via the injector interface 34. Following the calculated scan delay, the clinical scan is obtained using the previously established clinical scan protocol.

At 264, the data from the clinical scan is used to generate human readable images. In one example, a series of axial images is generated. In another example, one or more three dimensional rendered images are generated. Of course, still other types of images may be generated, such as sagittal, coronal, multiplanar reformatted (MPR), maximum intensity projection (MIP) images or image series may generated depending on the needs of particular situation.

At 268, the images are displayed on the operator console 30.

The techniques described above have application to various regions of the body. In CTA imaging of the pulmonary artery, for example, it may be desirable to selectively enhance both the pulmonary arteries and veins or only the arteries. Similarly, in CTA imaging of the carotid artery, it may be desirable to selectively enhance both the carotid artery and the jugular vein or only the carotid. In each case, the operator would select the relevant ROIs as either enhanced or nonenhanced ROIs. Suitable patient specific uniphasic or multiphasic injection profiles are readily calculated as described above.

Yet another application involves contrast enhanced imaging of the liver. The liver has two primary sources of blood supply—the hepatic artery and the portal vein. Biphasic liver scans typically include scan at the hepatic arterial phase and the portal venous phase. There are two primary types of triphasic liver scan—either early arterial phase followed by late arterial phase (about 5 sec later) and hepatic venous phase (some 20 sec after the late arterial phase), or a second type of triphasic liver scan—arterial phase followed by hepatic venous phase, followed by late enhancement phase or equilibrium phase (about 100-120 sec after injection) when attenuation values of arteries are low and the entire liver is enhanced. To perform a contrast enhanced scan of the liver, the tracking scan is preferably obtained at a location at the level of the liver where both the aorta and portal veins are visible. One or both of the aorta and the portal vein are then selected as the ROI(s) for the purpose or predicting the time enhancement profile, the scan delay, injection profile, and other relevant parameters. A multiphasic injection is performed, followed by a single scan as generally described above in connection with FIG. 7. While patient specific information is readily calculated as described above, an example of an approximate sequence and timing of a triphasic injection followed by a single CT scan is described below:

| | Time From Start (sec) | Time To Scan (sec) | Duration (sec) |
|---|---|---|---|
| Initiate Clinical Portion of Procedure | 0 | 120 | 0 |
| Start First Injection | 0 | 120 | 30 |
| Delay Between First and Second Injections | 30 | 90 | 25 |
| Start Second Injection | 55 | 65 | 25 |
| Delay Between Second and Third Injections | 80 | 40 | 15 |
| Start Third Injection | 95 | 25 | 15 |
| Delay Between Third Injection and Scan | 110 | 10 | 10 |
| Clinical Scan | 120 | 0 | 30 |

Still other variations are possible. Rather than establishing a single desired enhancement for multiple ROIs, it is possible to define different enhancement profiles for each, so that each ROI is enhanced, but to a different degree. The injection profile(s) are selected accordingly. The differing enhancements can then be used to segment the data among the various phases (e.g., arterial, venous, etc.) as an aide to differentiating the various vessels. In addition, the invention is not limited to CTA and may be performed in conjunction with magnetic resonance or other imaging modalities.

Of course, modifications and alterations will occur to others upon reading and understanding the preceding description. It is intended that the invention be construed as including all such modifications and alterations insofar as they come within the scope of the appended claims or the equivalents thereof.

What is claimed is:

1. A method comprising:

administering a contrast agent test injection to a patient according to a first injection profile prior to a selected diagnostic imaging procedure;

defining first and second regions of interest of the anatomy of the patient;

establishing a first desired time enhancement profile at the first region of interest and a second desired time enhancement profile at the second region of interest;

establishing a desired multiphasic injection profile for administering contrast agent to the patient, wherein the desired multiphasic injection profile is established based on the first and second desired time enhancement profiles, a first injection profile used to administer contrast agent to the patient, and measured time enhancement profiles at the first and second regions of interest resulting from the administration of the contrast agent to the patient according to the first injection profile;

wherein establishing the desired patient injection profile includes:

establishing a desired injection profile for enhancing the first region of interest, establishing a desired injection profile for enhancing the second region of interest; and wherein the desired patient injection profile for administering contrast agent to the patient is a multiphasic injection profile which includes the first desired injection profile for enhancing the first region of interest and the second desired injection profile for enhancing the second region of interest.

2. The method of claim 1 including coordinating the phases of the multiphasic injection profile so that the desired enhancements of the first and second regions of interest are predicted to occur at approximately the same time.

3. The method of claim 2 including:

administering contrast agent to the patient according to the desired injection profile;

obtaining a scan of the anatomy of the patient including an enhancement resulting from the administration of contrast agent to the patient according to the desired injection profile.

4. The method of claim 3 wherein the first and second desired time enhancement profiles include different enhancement values.

5. The method of claim 4 including generating volumetric image data indicative of the anatomy of the patient and segmenting the image data based on the enhancement.

6. The method of claim 2 wherein the first region of interest includes the aorta at the level of the liver and the second region of interest includes the portal vein and the step of obtaining a scan of the anatomy of the patient includes obtaining a scan of the liver.

7. A method comprising:
   administering a contrast agent test injection to a patient according to a first injection profile prior to a selected diagnostic imaging procedure;
   obtaining a plurality of test images including first and second regions of interest including an enhancement resulting from the administration of the contrast agent test injection according to the first injection profile;
   defining the first and second regions of interest of the anatomy of the patient from in the test images;
   establishing a first desired time enhancement profile at the first region of interest and a second desired time enhancement profile at the second region of interest;
   measuring time enhancement profiles at the first and second regions of interest resulting from the administration of the contrast agent test injection to the patient according to the first injection profile; and
   establishing a desired injection profile for administering contrast agent to the patient in the diagnostic imaging procedure based on the first and second desired time enhancement profiles, the first injection profile used to administer contrast agent to the patient, and the measured time enhancement profiles at the first and second regions of interest.

8. The method of claim 7 including defining a third region of interest of the anatomy of the patient, establishing a third desired time enhancement profile at the third region of interest, and establishing the desired injection profile based on the third desired time enhancement profile and a measured time enhancement profile at the third region of interest resulting from the administration of the contrast agent to the patient.

9. The method of claim 7 including using electrical signals to communicate the desired injection profile to a power contrast injector.

10. The method of claim 7 including segmenting the first and second regions of interest based on the enhancement resulting from the contrast agent.

11. The method of claim 10 wherein the desired enhancement profiles are established so that the first and second regions of interest are enhanced, but to a different degree.

12. The method of claim 7 including using a linear and time invariant model to establish the desired injection profile.

13. An apparatus comprising:
   one or more computer processors configured to:
      collect tracking scan information resultant from an application of a test contrast agent injection applied with a first injection profile administered prior to a diagnostic imaging procedure,
      receive identifications of first and second regions of interest of the anatomy of a patient,
      sample the collected tracking scan information at each of the defined first and second regions of interest,
      establish a first desired time enhancement profile at the first region of interest and a second desired time enhancement profile at the second region of interest the first and second desired time enhancement profiles being different from each other,
      identify a first measured time enhancement profile in the first region of interest and a second measured time enhancement profile in the second region of interest,
      establish a multiphasic injection profile for administering contrast agent to the patient in the diagnostic imaging procedure, the multiphasic injection profile having phases based on a combination of the first and second desired time enhancement profiles, the first injection profile and the first and second measured time enhancement profiles such that the desired enhancements in the first and second regions of interest occur concurrently during the diagnostic imaging.

14. A method comprising:
   defining a first region of interest of a patient's anatomy;
   establishing a desired enhancement profile for the first region of interest;
   administering a test injection of contrast agent to the patient according to a test injection profile;
   obtaining a tracking scan of the patient's anatomy, the tracking scan generating a plurality of temporally spaced images indicative of an enhancement resulting from administration of the contrast agent according to the test injection profile;
   using the plurality of temporally spaced images to generate a first measured enhancement profile at the first region of interest;
   establishing a first desired injection profile for administering contrast agent to the patient;
   predicting an enhancement of the first region of interest resulting from the first desired injection profile, wherein the prediction is based on the test injection profile, the first measured enhancement profile, and the first desired injection profile;
   communicating the first desired injection profile to the injector via electrical signals;
   administering contrast agent to the patient according to the first desired injection profile;
   obtaining a scan of the patient's anatomy enhanced by the contrast agent administered according to the first desired injection profile.

15. The method of claim 14 further including:
   using the first enhancement profile to calculate a scan delay period; and
   minimizing the scan delay period in accordance with a designation that the first scan region is a non-enhanced region of interest.

16. The method of claim 14 including fitting the first enhancement profile to an ideal time enhancement profile to generate a first corrected time enhancement profile and using the first corrected time enhancement profile to predict the enhancement of the first region of interest.

17. The method of claim 14 including:
   defining a second region of interest of the patient's anatomy;
   using the plurality of temporally spaced images to generate a second measured enhancement profile at the second region of interest;
   establishing a second desired injection profile for administering contrast agent to the patient;
   predicting an enhancement at the second region of interest resulting from the second desired injection profile, wherein the prediction is based on the test injection profile, the second enhancement profile, and the second desired injection profile.

18. The method of claim 17 including establishing a multiphasic injection profile which includes the first and second desired injection profiles, wherein the phases of the multiphasic injection are coordinated so that the enhancement of the first and second regions of interest are predicted to occur at approximately the same time.

19. The method of claim 18 wherein the first and second desired enhancement profiles include different enhancement values and wherein the method includes segmenting data from the scan according to enhancement values.

20. The method of claim 18 wherein the multiphasic injection includes three phases and wherein the method includes, in temporal order:
   administering the first phase of the multiphasic injection according to the first desired injection profile;
   waiting for a first time period;
   administering the second phase of the multiphasic injection according to the second desired injection profile;
   waiting for a second time period;
   administering a third phase of the multiphasic injection;
   waiting for a third time period;
   initiating the scan.

21. The method of claim 17 including using the test injection profile and the first enhancement profile to establish a first patient function at the first region of interest and using the test injection profile and the second enhancement profile to establish a second patient function at the second region of interest.

22. The method of claim 14 wherein the first and second desired enhancement profiles include different non-zero enhancement values and wherein the method includes segmenting data from the scan according to enhancement values.

23. A non-transitory computer readable medium carrying instructions which controls one or more computers to:
   receive an identification a first region of interest of a patient's anatomy and a second region of interest of the patient's anatomy;
   generate a first measured time enhancement profile at the first region of interest based on a plurality of temporally spaced test images of the patient's anatomy obtained following an injection of contrast agent according to a test injection profile;
   generate a second measured time enhancement profile at the second region of interest based on the plurality of temporally spaced test images of the patient's anatomy obtained following the injection of contrast agent according to the test injection profile;
   establish a first desired time enhancement profile at the first region of interest;
   establish a second desired time enhancement profile at the second region of interest;
   establish a multiphasic injection profile for administering contrast agent to the patient during a diagnostic procedure in which desired contrast enhancements are achieved in the first and second regions of interest, wherein the multiphasic injection profile is established based on the first and second desired time enhancement profiles, the test injection profile, and the first and second measured time enhancement profiles; and
   communicate the multiphasic injection profile to an injector via an electrical signal.

24. The non-transitory computer readable medium of claim 23, further carrying instructions which control the one or more computers to receive a human input indicative of the first and second regions of interest so as to identify the first and second regions of interest.

25. The non-transitory computer readable medium of claim 23 wherein the first and second desired time enhancement profiles are established so that the first and second regions of interest are both enhanced, but to a different degree.

26. The non-transitory computer readable medium of claim 25, wherein the multiphasic injection profile includes a first phase for enhancing the first region of interest and a second phase for enhancing the second region of interest, wherein the first and second phases are coordinated so that the desired enhancements of the first and second regions of interest are predicted to occur concurrently.

27. The non-transitory computer readable medium of claim 26, further carrying instructions which control the one or more computers to receive CT scan data indicative of the first and second regions of interest and distinguishing between the first and second regions of interest based on their observed enhancement.

28. A method comprising:
   prior to a diagnostic imaging procedure, administering contrast agent to a patient according to a test injection profile;
   obtaining a tracking scan of the patient's anatomy, the tracking scan generating a plurality of temporally spaced images indicative of an enhancement resulting from the administration of the contrast agent according to the test injection profile;
   establishing a first desired time enhancement profile for a first region of the liver and a second desired time enhancement profile for a second region of the liver including a first scan delay associated with the first desired time enhancement profile and a second scan delay associated with the second desired time enhancement profile;
   using information from the tracking scan and the first and second desired time enhancement profiles to establish a multiphasic injection profile for administering contrast to the patient for the diagnostic imaging procedure, wherein the multiphasic injection profile includes a first phase for enhancing the first region of the liver and a second phase for enhancing a second region of the liver;
   modifying at least one of the first scan delay and the second scan delay to ensure that the desired enhancements of the first and second regions of the liver are predicted to occur at approximately the same time;
   administering the contrast agent in accordance with the modified first and second scan delays based upon the established multiphasic injection profile; and
   obtaining a scan of the patient during the time at which the desired enhancements of the first and second regions of the liver are predicted to occur.

29. The method of claim 28 wherein the first region of the liver is a venous region and the second region of the liver is an arterial region.

30. The method of claim 28 wherein the method includes
   establishing a third desired time enhancement profile for a third region of the liver;
   using information from the third desired time enhancement profile to establish the multiphasic injection profile, wherein the multiphasic injection profile includes a third phase for enhancing the third region of the liver, and wherein the desired enhancements of the first, second, and third regions of the liver are predicted to occur at approximately the same time; and
   imaging at least the first, second, and third regions of the liver concurrently when the first, second, and third regions have the desired enhancements.

* * * * *